Figure 1:
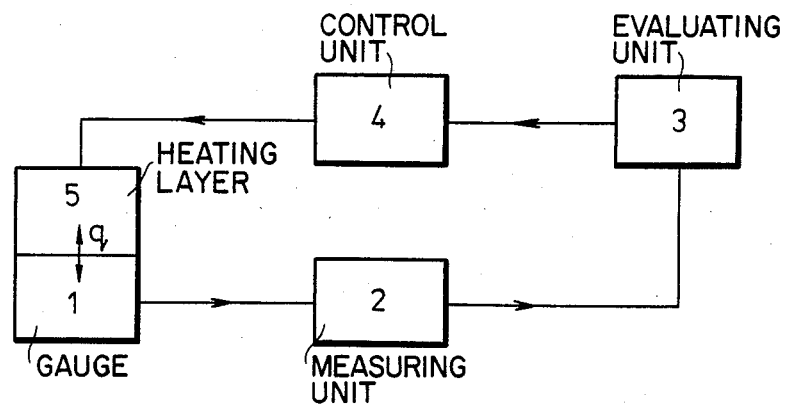

United States Patent [19]

Szabó et al.

[11] Patent Number: 4,568,198
[45] Date of Patent: Feb. 4, 1986

[54] METHOD AND APPARATUS FOR THE DETERMINATION OF THE HEAT TRANSFER COEFFICIENT

[75] Inventors: Imre Szabó ; György Dankó ; Zsolt I. Vitéz; György Kulin, all of Budapest, Hungary

[73] Assignee: Budapesti Muszaki Egyetem, Budapest, Hungary

[21] Appl. No.: 498,546

[22] Filed: May 26, 1983

[30] Foreign Application Priority Data

Jun. 3, 1982 [HU] Hungary .............................. 1781/82

[51] Int. Cl.$^4$ ............................................. G01N 25/18
[52] U.S. Cl. ..................................... 374/43; 364/557; 374/29
[58] Field of Search ........................ 374/43, 44, 29, 30, 374/114, 164; 364/557; 219/504

[56] References Cited

U.S. PATENT DOCUMENTS

| | | | |
|---|---|---|---|
| 3,238,775 | 3/1966 | Watts | 374/30 |
| 3,396,267 | 8/1968 | Dietrich | 364/557 X |
| 3,578,405 | 5/1971 | Woodle | 364/557 X |
| 3,971,246 | 7/1976 | Sumikama et al. | 374/44 |
| 4,246,468 | 1/1981 | Horsma | 219/505 X |
| 4,361,799 | 11/1982 | Lutz | 374/114 |
| 4,364,676 | 12/1982 | Oja et al. | 374/44 |

OTHER PUBLICATIONS

"The Possibility of Determining and Using a New Local Heat Transverse Coefficient", G. Danko, Int. J. Heat Mass Transfer, vol. 26, No. 11, pp. 1679–1684, 1983.

Primary Examiner—Daniel M. Yasich
Attorney, Agent, or Firm—Young & Thompson

[57] ABSTRACT

A method for the determination of the heat transfer coefficient on a heat transferring surface, including the steps of arranging a layer for measuring the surface temperature and heat flux on the heat transferring surface so that the layer can change the original temperature and heat flux to a negligible extent only, providing for the slight and properly slow changeability of the surface heat flux density within a cycle time which is by several orders of magnitude longer than the time constants of the heat flux measuring layer and of the heat transferring boundary layer, by using a supplementary heating element and performing a practically unlimited number of measuring cycles, using the steps of deflecting the surface heat flux density and temperature relative to the condition in which no measurement takes place. The time-functions of the changes of the surface temperature $\Delta T$ and of the surface heat flux density $\Delta q$ are determined, and the heat transfer coefficient is defined as the approximate limit value H of the quotients $\Delta q/\Delta T$ corresponding to the zero surface heat flux density or temperature deflection.

1 Claim, 2 Drawing Figures

METHOD AND APPARATUS FOR THE DETERMINATION OF THE HEAT TRANSFER COEFFICIENT

The invention relates to a method and an apparatus for the determination of the heat transfer coefficient. To practice the method a layer for measuring the surface temperature and the heat flux is arranged on the heat transferring surface which changes the original temperature and heat flux to a negligible extent only, and by regulating the power output used for heating and cooling the surface or by using an additional heating element provision is made for the fine and sufficiently slow cyclical adjustability of the surface heat flux density within a cycle time which is by several orders of magnitude longer than the time constants of the heat flux measuring layer and of the heat transferring boundary layer, which cycle time is e.g. 60 sec, and measuring cycles are performed and the maximum number of the cycles is essentially unlimited.

It is known in the art that accurate knowledge of the surface heat transfer coefficient is required in several cases. In some cases either an intensive surface heat transfer and consequently a large surface heat flux density is required with low costs, or quite to the contrary a low heat transfer is wanted also with low costs. In other cases the knowledge of the heat transfer coefficients is needed for planning the required useful life and operational safety. In the majority of the cases for the efficient thermal design the knowledge of the local distribution of the heat transfer coefficient is also required.

The requirements relating to the heat transfer coefficient resulted in a rapid development in the fields of both experimental and theoretical activities. However, in recent years the rapid, nearly disproportionate development of the computerized simulation compared to experimental techniques can be observed. One for the reasons of this phenomenon lies in the obvious and long term advantages of simulation, namely in its applicability in the phase of planning without the need of making preliminary experiments. There are other problems connected with the measurement of the heat transfer coefficient of which some should be particularly mentioned as follows:

(a) For the usually defined heat transfer coefficient one has to define—relatively arbitrarily—a so-called infinite remote boundary layer temperature T; this arbitrary property is carried by the measured heat transfer coefficient, which cannot therefore be considered any more as a real system characteristic. This reduces the accuracy and limits the possibilities of generalization.

(b) In addition to the abovementioned theoretical error the measurement of the infinite remote temperature involves certain difficulties, and for its determination the temperature profile of the whole boundary layer must be known.

(c) It can be supposed that the aforesaid reason can explain why no compact measuring system is available on the market for measuring the heat transfer coefficient. The current measuring practice can be characterized by individually designed measuring instruments and by the application of diverse measuring theories.

In addition to the general disadvantages mentioned above, the known measuring principles and methods have further advantageous and disadvantageous features. These features can be summarized as follows:

The so-called sublimation measuring method utilizing the analogy of heat and mass transfer, can be most advantageously used for the determination of the surface distribution of the heat transfer coefficient on the surface, if experiments can be performed with an unheated model. In heated equipment with changing temperatures this method cannot be used. The evaluability of sublimation measuring methods is also dubious which relates only to a small portion of a large surface, since in analogous system this situation corresponds to the case of thermal entrance.

In the classical basis measuring method which measures the surface heat flux density by means of measuring gauges or by any other ways and which determines the difference between the surface temperature $T_f$ and the infinite remote temperature $T_\infty$ also by measurements, when the temperature difference $T_f - T_\infty$ is small, even slight fluctuations of the temperature $T_\infty$ of the medium might result in high measuring errors. The fluctuations of the temperature $T_\infty$, which temperature represents a temperature outside the boundary layer, are less attenuated than the fluctuations of the heat transfer coefficient.

There are well known methods which completely eliminate ambient temperature and the measuring problems connected therewith. Their common characteristics are that a measuring probe is placed on the surface which can be either a built in or a separately attached model, and the probe is heated and on the basis of the cooling curve, a calculation is made to determine or a comparison is made with a known calibration curve to conclude the value of the heat transfer coefficient on the probe and thus on the original surface. The common characteristic of such transient methods lies in that the measuring probes function as transient heat flux density meters and the change in the heat quantity introduces by the heating during the measuring process is sensed only on the basis of the change of the probe temperature with time as a sole parameter.

The measurement of the heat flux density streaming through the measuring probe or of the original undisturbed heat flux density is not considered to be necessary and it is not even tried. In the evaluation of the measuring results the heat capacity of the measuring probe plays an important role, and proper heat insulation between the probe and the original surface may decrease the unavoidable measuring errors. A common drawback is, that since quick transients cannot be allowed from the side of the boundary layer, the measuring probes are too thick and have large masses. These complicated methods which often require calibrations, are inconvenient and compared to the difficulties their information content is rather modest. Although the measurements are free of the ambient temperature T, at the same time they are not suitable at all for the determination thereof.

The object of the invention is the elimination of the above mentioned drawbacks.

The main characteristics of the method according to the invention and the apparatus for the realization thereof are as follows:

1. As a heat transfer coefficient a real system characteristic is identified, accordingly it is free from the disadvantages according to point (a).
2. Although the determination of the heat transfer coefficient does not require the knowledge of the temperature $T_\infty$, this latter can also be determined without measuring the temperature of the boundary layer. The value of $T_\infty$ evaluated on the basis of measurement also is a system characteristic. Accordingly, the method is free from the disadvantage specified in point (b), too.
3. The measuring method uses compact equipment and a measuring probe. In appearance, the measuring probe is identical with the thin foil-type heat flux measuring gauges.
4. By using the same equipment and measuring probe, together with the measurement of the heat transfer coefficient and the temperature $T_\infty$ of the boundary layer, the surface heat flux density q and the surface temperature $T_f$ can also be measured.
5. Both the method and the equipment are suitable for measuring not only the usually defined "technical" heat transfer coefficient but also the local "physical" heat transfer coefficient defined recently in the technical literature and publications.

In order to be able to ensure the properties listed hereinabove, the essence of the method according to the invention lies in that on the heat transferring surface to be examined a layer for measuring the surface temperature and heat flux is arranged which changes the original temperature and heat flux to a neglibile extent only, further provision is made by regulating the output power of the means heating or cooling the surface or by using a supplementary heating element to establish a slight and properly slow cyclical change of the surface heat flux density within a cycle time which is longer by several orders of magnitude than the time constants of the heat flux measuring layer and of the heat transferring boundary layer, e.g. within 60 sec, and carrying out the measurement during a practically unlimited number of cycles.

In accordance with the invention the measuring cycles are performed in such a manner that the surface heat flux density and the temperature are detected during the consecutive cycles relative to the condition in which no measurement takes place, thereafter the process is repeated and during the respective cycles the time-functions of the change of the real surface temperature $\Delta T$ and of the surface heat flux density $\Delta q$ are determined, and the heat transfer coefficient which is to be determined is supposed to be identical with approximate limit values H of the cyclically changing quotients $\Delta q/\Delta T$ which belong to the zero change in surface heat flux density or temperature changes, while the approximate limit values H belonging to the zero surface heat flux density or temperature deviations are determined from the functions $\Delta T$ and $\Delta q$ changing in time during the respective cycles.

The apparatus for the realization of the method according to the invention i.e. the circuit arrangement is also an aspect of the present invention. The circuit arrangement for measuring the heat transfer coefficient comprises a temperature and heat flux measuring layer arranged on the surface to be measured, a unit coupled to this layer for measuring the surface temperature and the heat flux density, as well as a measurement organizing and evaluating unit connected to the output of the previously mentioned unit, and the arrangement can be characterized in that to the output of the measurement organizing and evaluating unit an input of an intervening unit controlling the cyclical changes of the heat flux density is connected and the output thereof is connected to a regulator element or to a supplementary heating element influencing the heat flux density of the surface examined.

The method according to the invention will now be described in connection with some exemplary alternative embodiments arranged in application orientated groups following an explanation of its theoretical background.

I. On the portion of the full examined surface containing the temperature and heat flux measuring layer examined by the surface of the measuring probe, the usual "technical" heat transfer coefficient can be measured, when in course of the measuring process we are interferring with the condition without measurement by changing the heat flux of the total heat transmitting surface in the course of deflecting and returning cycles. Interference must be quasi-stationary, that means, that the changes in temperature and heat flux density belonging to the transient generated in the thermal boundary layer must not deviate considerably from the values belonging to the infinitely slow changes. For simpler evaluations of the measuring results it seems to be expedient to maintain the quasi-stationary condition also for the heat flux measuring and temperature measuring layer. That means, that the measured and actual values of $\Delta T$ and $\Delta q$ can be taken as identical. This requirement—expressed by means of the time constants—means that the cycle time of the changes should be longer by several orders of magnitude than the longer one of the time constants of the heat flux measuring layer and the heat transferring boundary layer. Within the respective cycle times, for the average time constant of the time-function of temperature or heat flux density during the deflections and return cycles it is already allowed and moreover, it is even expedient, if it is of the same order of magnitude, as the cycle time. Essentially, this latter time constant corresponds to the resultant average time constant of the examined surface point and of the measuring probe, and its value is generally high in relation to the previously mentioned two time constants. The generation of the changes which fill the cycle times with exponentially increasing and decreasing sections in a saw-tooth like manner which act on a surface element having a large time-constant, can be performed by switching the heating current deflection on and off during the deflection and return cycles. On basis of the uniform and suitably slow changes in the time domain it will be possible to determine the real value of the heat transfer coefficient which corresponds to zero disturbance. In order to be able to maintain this advantage, when a surface element is measured which has a low time constant, for obtaining uniform and slow changes within the respective cycle times, a uniformly and slow increasing heat flux deflection is required within the deflection cycles while in the return cycles a return control is necessary which provides a monotonously decaying return process.

The deflection of the heat flux can be effected by the control of the output power cooling or heating the examined surface or by the use of a supplementary heating element. The control of the heating or cooling output power can be effected e.g. by regulating an electric power source or, when the heat transfer medium is saturated steam or a liquid, by controlling the saturation temperature or the temperature of the medium. If there is no means available which could change the heating or cooling power, a supplementary heating element should be arranged on the surface to be examined. If the supplementary heating element covers the whole surface, the usual local "technical" heat transfer coefficient can be measured at any small part of the surface, no matter how small it is. In the method according to the invention the heat transfer coefficient which should be determined can be calculated from the measured values of the surface temperature and the heat flux density determined during the deflection and return cycles. For the calculations, i.e. for the evaluation of the measurements, the ratio $\Delta q/\Delta T$ is used defined by the changes in the heat flux density $\Delta q$ and in the temperature $\Delta T$ in relation to the static condition, which ratio can also fluctuate in time. This is done in such a way that the heat transfer coefficient to be determined is supposed to be identical with the approximate limit value H of the ratio which corresponds to the zero temperature or heat flux density deflection. In the simplest cases, e.g. when low temperature and heat flux density deflections (e.g. max. 5%) are generated, the approximate limit value H can be considered to be identical with the average of the ratio $\Delta q/\Delta T$ determinable in the respective measuring cycles. The determination of the average ratio $\Delta q/\Delta T$ can be done by known ways from the measuring results obtained for $\Delta q$ and $\Delta T$, by the distortion-free suppression of the measuring noise supposed to be of additive character. In anouther simple case, e.g. when a larger total deflection (e.g. 100%) of temperature and heat flux density is generated, the approximating limit value H can be considered as identical with the average quotient $\Delta q/\Delta T$ which can be determined for the phases with decelerated change of the respective measuring cyles.

In general the approximating limit value H is identical with the extrapolated value of the quotient $\Delta q/\Delta T$ which varies in time and which limit value is supposed to correspond to the zero-values of $\Delta q$ and $\Delta T$. For the extrapolation the condition and the time of the zero deflections can be determined from the time functions $\Delta q$ and $\Delta T$ of the deflecting and return cycles. Due to the finite heat capacity of the heat flux measuring layer and of the surface temperature meter, and due to the non-zero changing speed, the measured and the actual values of $\Delta T$ and $\Delta q$ will be different. In a time-saving measuring process which has a quasistationary character in relation not only to the thermal boundary layer but also to the measuring probe, if the required accuracy makes it necessary, the distorting effect of the heat capacity of the heat flux measuring layer on the results of the measurement can be eliminated. In this case the thermal system identification of the heat flux measuring layer and the surface temperature measuring system should be carried out, which layer and system are characterized by the known geometry and by the known thermal-physical parameters, which identification is made unambiguous by means of an unknown parameter $\Delta q/\Delta T$ as an extreme condition so that it should be in conformity with the measuring results obtained for $\Delta q$ and $\Delta T$. The quotient $\Delta q/\Delta T$ which can be determined in such a manner, represents theorically the optimal approximation for the approximating limit value H.

The ambient temperature can be determined from the values of the undisturbed surface temperature and heat flux density and from the measured value of the heat transfer coefficient determined by measurement in such a manner that the value of the surface temperature is considered as th the ambient temperature $T_\infty$, which is decreased in correct sign by the ratio of the surface heat flux density and the heat transfer coefficient. The temperature $T_\infty$ of the medium determined in the described manner satisfies, of course, the basic formula of heat transfer.

II. On the portion of the examined full surface examined by the measuring probe containing the temperature and heat flux measuring layer, the "physical" heat transfer coefficient can be measured, if during the measuring process intervention is made by cyclically changing the heat flux as described in point I above only on a surface-portion corresponding substantially to the surface of the measuring probe. This measuring process corresponds to that of point I.

In order to decrease the distorting effect ("edge effect") of the heat flux components in the boundary layer parallel to the surface, it proved to be expedient to decrease slightly the size of the heat flux measuring layer compared to that of the heating surface. For measuring the "physical" heat transfer coefficient a compact measuring probe provided with an electric heating layer can be used. One of the main advantages of the "physical" heat transfer coefficient lies just in this fact.

III. Theoretically the local "physical" heat transfer coefficient can be measured only with a heating surface having a zero-size, in which the uncompensable "edge effect" would only the measuring process. Instead of this a practically well realizable method is used, in which a small measuring probe comprising a heat flux measuring patch is used as a gauge, being preferably 0.2 mm thick and having a size of 1-20 mm. Furthermore, there is used a heating element which can be activated on a surface variable in size in relation to the size of the patch, expediently by 1.2 ... 5-fold thereof, and a thermometer. The measurement of the heat transfer coefficient is repeatedly carried out on heated surfaces of various sizes, and the extrapolated limit value belonging to the zero-surface is considered to be identical with the local "physical" heat transfer coefficient. The so obtained parameter represents a system-characteristic independent of the surface of the measuring probe. The ambient temperature T, which can be calculated together with the local physical heat transfer coefficient in accordance with point I, represents also a significant system characteristic. The above described measuring methods can be used both for obtaining individual measuring results and for continuous measurements. For obtaining individual measuring results the application of several subsequent measuring cycles may also be useful to ensure reliable statistical evaluating possibilities.

As already mentioned before, the apparatus for carrying out the method according to the invention also forms the subject of the present invention.

Figure 2:
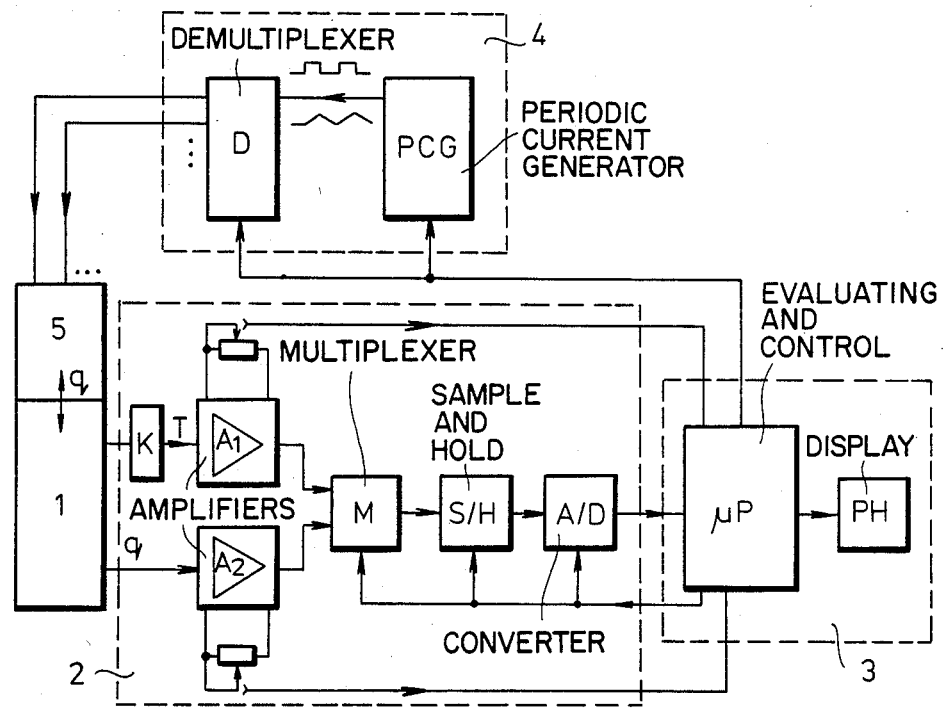

The invention will now be described in detail by means of a preferred embodiment thereof, in which reference will be made to the drawing, wherein FIG. 1 is the schematic block diagram of the circuit arrangement of the equipment according to the invention, FIG. 2 is a more detailed schematic diagram of the blocks shown in FIG. 1.

The equipment for carrying out the method according to the invention will now be described on the basis of the block diagram shown in FIG. 1. The electrical terminals of the gauge or probe measuring the surface temperature and the heat flux are connected to the input of a measuring unit 2 of surface temperature and heat flux density while the—expediently digital—output of said unit 2 is connected to a unit 3 organizing and evaluating the measuring process.

The equipment as described hereinabove corresponds to the known measurement data acquisition equipment widely used for measuring the temperature and the heat flux. The novelty of the proposed circuit arrangement lies in that the unit 3 organizing and evaluating the measuring process is coupled to an intervention unit 4 controlling the cyclic change of the heat flux density and its output is thermally fed back to the regulator element controlling the heat flux density of the examined surface or to the supplementary heating layer 5 of the measuring probe.

The layout of the single partial units of the equipment according to the invention may be of the most diverse formation. An expedient embodiment is shown in FIG. 2, in which the unit 2 measuring the surface temperature and the heat flux comprises analog amplifiers $A_1$ and $A_2$ which are connected to the input terminals of the units 2 and comprising zero-point and sensitivity adjusting elements, a multiplexer M connected to the respective outputs of the amplifiers, a sample and hold circuit S/H coupled to the multiplexer M, and an analog/digital converter A/D. The unit 3 organizing and evaluating the measuring process comprises an evaluating and control unit $\mu$P, a display unit PH connected thereto, and a periphery-drive and/or a recording-unit for registering the results obtained. The intervention unit 4 controlling the cyclic change of the heat flux density comprises a conventional commercially-available periodical electric current-function generator PCG and a demultiplexer D connected thereto for the direct drive of supplementary heating elements of different sizes. Ahead of the analog amplifier $A_1$, and optional zero-point thermostat K can be inserted for measuring the temperature by means of a thermoelement. A preferred embodiment of the measuring equipment can be achieved if the periodical electric current-function generator PCG is a programmable square-wave generator in the case of surfaces with a high thermal time constant, and is a saw-tooth current generator measuring in the use of surfaces with a small time constant, and the analog demultiplexer D can be programmed in accordance with the number of the output channels. The measuring detector which can be used for the measuring process comprises a surface temperature meter and a heat flux density measuring layer. The compact measuring probe used for measuring the "physical" heat transfer coefficient contains also an additional electric heating layer. The surface temperature meter is expediently a thermocouple connected through a cold-junction thermostat to the input of the unit measuring the temperature and the heat flux density.

Expediently the layer measuring the heat flux comprises a plurality of thermocouples connected in series, while the additional electric heating layer lies on the side of the measuring probe facing the surface to be measured and comprises a film-like or a sinuous electric heating element.

We claim:

1. A method of determining the heat transfer coefficient from a solid surface to a surrounding moving fluid medium, comprising disposing on the surface to be tested a measuring gauge which is flat and thin and comprises a layer for measuring surface temperature and heat flux density, providing a supplemental heating layer in the form of an electrical resistance, said supplemental heating layer being larger than said measuring layer and mounted between said measuring layer and said surface to be tested, cyclically changing the surface heat flux density over a plurality of cycles each of which has a period which is several orders of magnitude longer than the thermal time constant of the heat flux and surface temperature measuring layer by alternately energizing and de-energizing said supplemental heating layer, measuring at a plurality of times the incremental changes $\Delta T$ in the surface temperature and incremental changes $\Delta q$ in the surface heat flux density with respect to time, and determining said heat transfer coefficient as the limit value of the quotients of $\Delta q/\Delta T$ as $\Delta T$ or $\Delta q$ approaches zero.

* * * * *